(12) United States Patent
McFerran (10) Patent No.: US 7,887,574 B2
(45) Date of Patent: Feb. 15, 2011

(54) STENT DELIVERY CATHETER

(75) Inventor: Sean McFerran, Newark, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 969 days.

(21) Appl. No.: 10/746,516

(22) Filed: Dec. 23, 2003

(65) Prior Publication Data

US 2005/0149160 A1 Jul. 7, 2005

(51) Int. Cl.
*A61F 2/06* (2006.01)
(52) U.S. Cl. .................................... 623/1.11
(58) Field of Classification Search ............... 623/1.2, 623/1.1, 1.11–1.54; 606/191, 192, 194, 99, 606/108, 200, 113, 114, 127, 128, 195–199
See application file for complete search history.

(56) References Cited

U.S. PATENT DOCUMENTS

| | | | |
|---|---|---|---|
| 4,547,194 A | 10/1985 | Moorehead | |
| 4,572,186 A | 2/1986 | Gould et al. | |
| 4,732,152 A | 3/1988 | Wallsten et al. | |
| 4,848,343 A | 7/1989 | Wallsten et al. | |
| 4,990,151 A | 2/1991 | Wallsten | |
| 5,026,377 A | 6/1991 | Burton et al. | |
| 5,089,006 A * | 2/1992 | Stiles .................... | 623/1.1 |
| 5,129,887 A | 7/1992 | Euteneuer et al. | |
| 5,192,297 A * | 3/1993 | Hull .................... | 623/1.11 |
| 5,201,757 A | 4/1993 | Heyn et al. | |
| 5,290,248 A | 3/1994 | Bierman et al. | |
| 5,324,269 A | 6/1994 | Miraki | |
| 5,360,401 A | 11/1994 | Turnland | |
| 5,389,087 A | 2/1995 | Miraki | |
| 5,391,172 A | 2/1995 | Williams et al. | |
| 5,409,495 A | 4/1995 | Osborn | |
| 5,433,723 A * | 7/1995 | Lindenberg et al. ......... | 606/198 |
| 5,458,605 A | 10/1995 | Klemm | |
| 5,458,615 A | 10/1995 | Klemm et al. | |
| 5,484,444 A | 1/1996 | Braunschweiler et al. | |
| 5,507,768 A | 4/1996 | Lau et al. | |
| 5,533,968 A | 7/1996 | Muni et al. | |
| 5,534,007 A | 7/1996 | St. Germain et al. | |
| 4,655,771 A | 9/1996 | Wallsten | |
| 5,558,101 A | 9/1996 | Brooks et al. | |

(Continued)

FOREIGN PATENT DOCUMENTS

DE 198 19 634 A1 11/1989

(Continued)

OTHER PUBLICATIONS

U.S. Appl. No. 10/764,054 to Henry et al., filed Jan. 23, 2004.

*Primary Examiner*—Anhtuan T Nguyen
*Assistant Examiner*—Kathleen Sonnett
(74) *Attorney, Agent, or Firm*—Vidas, Arrett & Steinkraus, P.A.

(57) ABSTRACT

A self-expanding stent delivery assembly includes an elongate member with a proximal region and a distal region. The distal region has an outer tubular member. A self-expanding stent is disposed within the outer tubular member. Circumferential movement of at least a portion of the proximal region causes relative axial movement between the self-expanding stent and the outer tubular member, deploying the stent. Methods of deploying a self-expanding stent are also described.

9 Claims, 7 Drawing Sheets

U.S. PATENT DOCUMENTS

| | | | |
|---|---|---|---|
| 5,571,168 A | 11/1996 | Toro | |
| 5,579,780 A | 12/1996 | Zadini et al. | |
| 5,591,172 A | 1/1997 | Bachmann et al. | |
| 5,690,644 A * | 11/1997 | Yurek et al. | 623/1.11 |
| 5,690,645 A | 11/1997 | Van Erp | |
| 5,695,499 A * | 12/1997 | Helgerson et al. | 606/108 |
| 5,709,703 A | 1/1998 | Lukie et al. | |
| 5,743,874 A | 4/1998 | Fischell et al. | |
| 5,772,669 A | 6/1998 | Vrba | |
| 5,776,142 A | 7/1998 | Gunderson | |
| 5,782,855 A | 7/1998 | Lau et al. | |
| 5,797,952 A | 8/1998 | Klein | |
| 5,807,327 A | 9/1998 | Green et al. | |
| 5,843,028 A | 12/1998 | Weaver et al. | |
| 5,921,968 A | 7/1999 | Lampropoulos et al. | |
| 5,921,971 A | 7/1999 | Agro et al. | |
| 5,980,532 A | 11/1999 | Wang | |
| 5,980,533 A | 11/1999 | Holman | |
| 5,989,280 A | 11/1999 | Euteneuer et al. | |
| 6,007,522 A | 12/1999 | Agro et al. | |
| 6,007,543 A | 12/1999 | Ellis et al. | |
| 6,059,752 A | 5/2000 | Segal | |
| 6,074,398 A | 6/2000 | Leschinsky | |
| 6,077,295 A * | 6/2000 | Limon et al. | 623/1.11 |
| 6,113,607 A | 9/2000 | Lau et al. | |
| 6,117,140 A | 9/2000 | Munsinger | |
| 6,120,522 A | 9/2000 | Vrba et al. | |
| 6,228,110 B1 | 5/2001 | Munsinger | |
| 6,235,051 B1 | 5/2001 | Murphy | |
| 6,287,329 B1 | 9/2001 | Duerig et al. | |
| 6,302,893 B1 | 10/2001 | Limon et al. | |
| 6,322,586 B1 | 11/2001 | Monroe et al. | |
| 6,342,066 B1 | 1/2002 | Toro et al. | |
| 6,383,344 B1 | 5/2002 | Miller et al. | |
| 6,391,051 B2 | 5/2002 | Sullivan, III et al. | |
| 6,398,802 B1 | 6/2002 | Yee | |
| 6,425,898 B1 | 7/2002 | Wilson et al. | |
| 6,428,566 B1 | 8/2002 | Holt | |
| 6,471,718 B1 | 10/2002 | Staehle et al. | |
| 6,478,814 B2 | 11/2002 | Wang et al. | |
| 6,494,889 B1 | 12/2002 | Fleischman et al. | |
| 6,514,261 B1 | 2/2003 | Randall et al. | |
| 6,517,548 B2 | 2/2003 | Lorentzen Cornelius et al. | |
| 6,530,947 B1 | 3/2003 | Euteneuer et al. | |
| 6,554,848 B2 | 4/2003 | Boylan et al. | |
| 6,576,006 B2 | 6/2003 | Limon et al. | |
| 6,582,460 B1 | 6/2003 | Cryer | |
| 6,592,549 B2 | 7/2003 | Gerdts et al. | |
| 6,607,551 B1 | 8/2003 | Sullivan et al. | |
| 6,613,075 B1 | 9/2003 | Healy et al. | |
| 6,623,491 B2 | 9/2003 | Thompson | |
| 6,623,518 B2 | 9/2003 | Thompson et al. | |
| 6,656,212 B2 | 12/2003 | Ravenscroft et al. | |
| 6,656,213 B2 | 12/2003 | Solem | |
| 6,660,030 B2 * | 12/2003 | Shaolian et al. | 623/1.11 |
| 6,663,660 B2 | 12/2003 | Dusbabek et al. | |
| 6,723,071 B2 | 4/2004 | Gerdts et al. | |
| 2001/0044648 A1 | 11/2001 | Wolinsky et al. | |
| 2002/0111666 A1 | 8/2002 | Hart et al. | |
| 2003/0074045 A1* | 4/2003 | Buzzard et al. | 623/1.11 |
| 2003/0093146 A1* | 5/2003 | Parodi | 623/1.36 |
| 2003/0153941 A1 | 8/2003 | Rourke | |

FOREIGN PATENT DOCUMENTS

| | | |
|---|---|---|
| EP | 0 505 686 A1 | 9/1992 |
| EP | 0 627 201 B1 | 12/1994 |
| EP | 0 873 733 A1 | 10/1998 |
| WO | WO 98/11846 | 3/1998 |
| WO | WO 99/49808 A1 | 10/1999 |
| WO | WO 00/67675 | 11/2000 |
| WO | WO 00/69498 A1 | 11/2000 |

* cited by examiner

STENT DELIVERY CATHETER

FIELD OF THE INVENTION

The present invention is related generally to medical devices. More specifically, the present invention is related to catheters. The present invention includes a stent delivery catheter apparatus for deployment of a self-expanding stent that has been loaded onto the catheter.

BACKGROUND OF THE INVENTION

Atherosclerotic disease is a leading cause of death in the industrialized world, particularly in the United States. Many heart attacks and strokes are caused in part by a narrowed, stenosed blood vessel. A medical procedure commonly used to deal with vessel stenosis is angioplasty. Angioplasty, in particular Percutaneous Transluminal Angioplasty (PTA), includes inserting a balloon catheter into the femoral artery near the groin, and advancing the catheter to the stenosis. The balloon can then be inflated to widen or dilate the narrowed region. The balloon catheter can then be withdrawn. In some cases, the widened vessel rebounds or re-closes, narrowing the vessel over a period of time.

Stents have come into increasing use to prevent the widened vessel regions from narrowing after angioplasty. A stent, typically having a tubular shape, can be put in place in the widened vessel region to hold the vessel walls apart and the lumen open in the event the conditions would otherwise result in re-stenosis. One class of stents requires that the stent be forcibly outwardly expanded to put the stent into position against the vessel walls. Another class of stents, self-expanding stents, can be delivered to a site in a compressed or constrained configuration and released in the vessel region to be supported. The self-expanding stent then expands in place to a configuration having a wide lumen, typically pressing firmly against the vessel walls where released. The stent is commonly placed at a recently dilated, stenosed vessel region.

Self-expanding stents can be delivered to a target site mounted over an inner tube or shaft and constrained within the distal end of an enclosing retractable tube or sleeve. The self-expanding stent can be freed from the restraint of the outer sheath by either distally pushing the inner shaft against the stent or proximally pulling the retractable outer sheath from over the stent. Once free of the outer restraint, the self-expanding stent can expand to force itself against the vessel inner walls. Self-expanding stents are often elastically biased to assume an original larger shape after being temporarily compressed into a smaller size to more easily be transported through blood vessels to the target site. There is an ongoing need for improvements in catheters that deliver self-expanding stents.

SUMMARY OF THE INVENTION

Generally, the present invention relates to a stent delivery device having helically engaged inner and outer members in which one or both are rotated for deploying a self-expanding stent from the stent delivery device. During rotation, the helical engagement causes relative axial movement between the inner and outer members to expose the stent which is positioned inside the outer member and in end-to-end contact with the inner member.

In one embodiment, a self-expanding stent delivery assembly includes an elongate member with a proximal region and a distal region. The distal region has an outer tubular member. A self-expanding stent is disposed within the outer tubular member. Circumferential movement of at least a portion of the proximal region causes relative axial movement between the self-expanding stent and the outer tubular member, deploying the stent. Methods of deploying a self-expanding stent are also described.

The above summary of the present invention is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE PREFERRED EMBODIMENTS

The stent delivery device and method for using the stent delivery device of the present invention are believed to be applicable to a variety of applications where delivery of stents is desired, for example, atherosclerotic stent delivery. While the present invention is not so limited, an appreciation of various aspects of the invention will be gained through a discussion of the examples provided below.

The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Also, while the tubular members illustrated in the Figures have generally circular cross sections, this is not a necessary part of the present invention, and the tubular members are merely shown as such for purposes of simplicity in illustration.

Figure 1A:
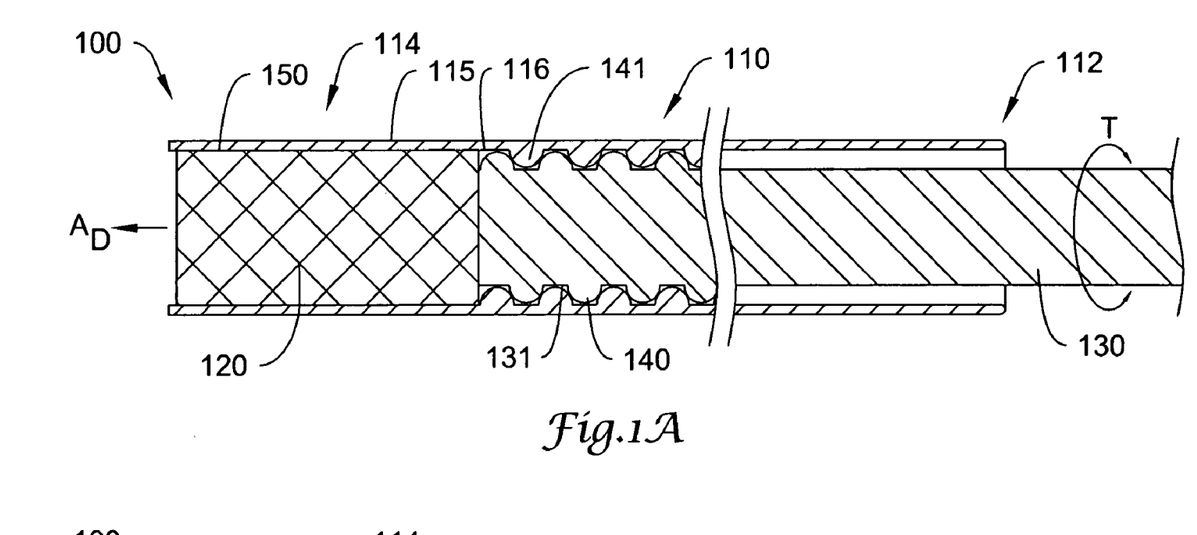
FIG. 1A is a schematic cross-sectional view of an illustrative stent delivery assembly.

FIG. 1A is a schematic cross-sectional view of an illustrative stent delivery assembly 100. The stent delivery assembly 100 can include an elongate member 110. The elongate member 110 can be, for example, a catheter. The elongate member 110 has a proximal region 112 and a distal region 114. At least a portion of proximal region 112 can remain outside of a patient's vasculature. At least a portion of the distal region 114 can remain inside the patient's vasculature. The elongate member 110 is any usable length such as, for example, 10 to 500 cm, 50 to 300 cm, or 75 to 200 cm. The elongate member 110 can be formed of any material suitable for delivering a stent through tortuous vessel passages such as, for example, a polymer, a metal, or a combination thereof. Exemplary materials include polyethylene, reinforced polyethylene, nylon, reinforced nylon, polyurethanes, reinforced polyurethanes, polyamides, or reinforced polyamides.

In an illustrative embodiment, a guidewire (not shown) can be optionally employed to guide the elongate member 110 distal region 114 to a target site within a patient's vasculature. The guidewire can be within a portion of the elongate member 110. The guidewire can be any operable diameter such as, for example, 0.01 to 0.04 inch or 0.014 to 0.035 inch.

In the illustrative embodiment, the elongate member 110 can have an outer tubular member 115 located at the distal region 114. A self-expanding stent 120 can be disposed within at least a portion of the outer tubular member 115. The outer tubular member 115 has an inner diameter sufficient in size to receive a compressed stent 120. The outer tubular member 115 can be formed of materials similar to those described above for forming the elongate member 110. In addition, an optional inner layer 150 of lubricious material can be disposed between the stent 120 and outer tubular member 115. The inner layer 150 can be formed of polytetrafluoroethylene, for example.

In an illustrative embodiment, the outer tubular member 115 can be any material as described above such as, for example, a clear medical grade PTFE (polytetrafluoroethylene) extrusion, which covers the distal 2-20 cm (depending on stent length) of the stent delivery device 100. However, the outer tubular member could be made of any suitable material as described above. A specific alternative embodiment could utilize a fluoropolymer material which is substantially transparent to visible light to enable an operator to directly view deployment in an endoscopic delivery procedure.

In an illustrative embodiment, self-expanding nitinol stents of from 1-15 mm or 6-14 mm in diameter and ranging from 1-100 mm or 5-50 mm in length can be accommodated. The self-expanding stent 120 can be formed from any material such as, for example, nitinol or stainless steel. The stent 120 can include one or more radiopaque markers for alignment into the target vessel. The stent 120 can be compressed at a low temperature for loading into delivery system 100 and held in its reduced delivery configuration by the outer tubular member 115. In the case of nitinol, upon deployment in vivo at body temperature, the original stent shape can be restored as the nitinol stent self-expands, exerting radial force on the constricted portion of the body lumen to re-establish patency.

The elongate member 110 can include an inner elongate member 130 disposed within at least a portion of the elongate member 110. The inner elongate member 130 can be formed of a polymer, a metal, or a combination thereof, as described above. The inner elongate member 130 can include a helical engagement element 140 on at least a portion of the inner elongate member 130. The helical element 140 can be a helical protrusion extending away from the outer surface 131 of the inner elongate member 130, or the helical element 140 can be a helical channel formed into the outer surface 131 of the inner elongate member 130. A helical engagement element 141 can be on at least a portion of the elongate member 110 inner surface 116. The helical engagement element 141 can be a single protrusion extending away from the elongate member 110 inner surface 116 toward the inner elongate member 130, or the helical engagement element 141 can be a continuous or non-continuous helical protrusion extending away from the elongate member 110 inner surface 116 toward the inner elongate member 130.

Alternatively, the elongate member 110 can include a helical engagement element 140 on at least a portion of the elongate member 110. The helical element 140 can be a helical protrusion extending away from the inner surface 116 of the elongate member 110, or the helical element 140 can be a helical channel formed into the inner surface 116 of the elongate member 110. A helical engagement element 141 can be on at least a portion of the inner elongate member 130 inner surface 131. The helical engagement element 141 can be a single protrusion extending away from the inner elongate member 130 outer surface 131 toward the elongate member 110, or the helical engagement element 141 can be a continuous or non-continuous helical protrusion extending away from the inner elongate member 130 outer surface 131 toward the elongate member 110.

The helical engagement element 141 is arranged and configured to engage the helical element 140 and convert at least a portion of circumferential movement T of the inner elongate member 130 into axial movement $A_D$. In this embodiment, rotational movement T of the inner elongate member 130 forces the inner elongate member 130 against the self-expanding stent 120 and pushes the self-expanding stent 120 axially in a distal direction $A_D$ relative to the outer tubular member 115, deploying the stent.

Figure 1B:
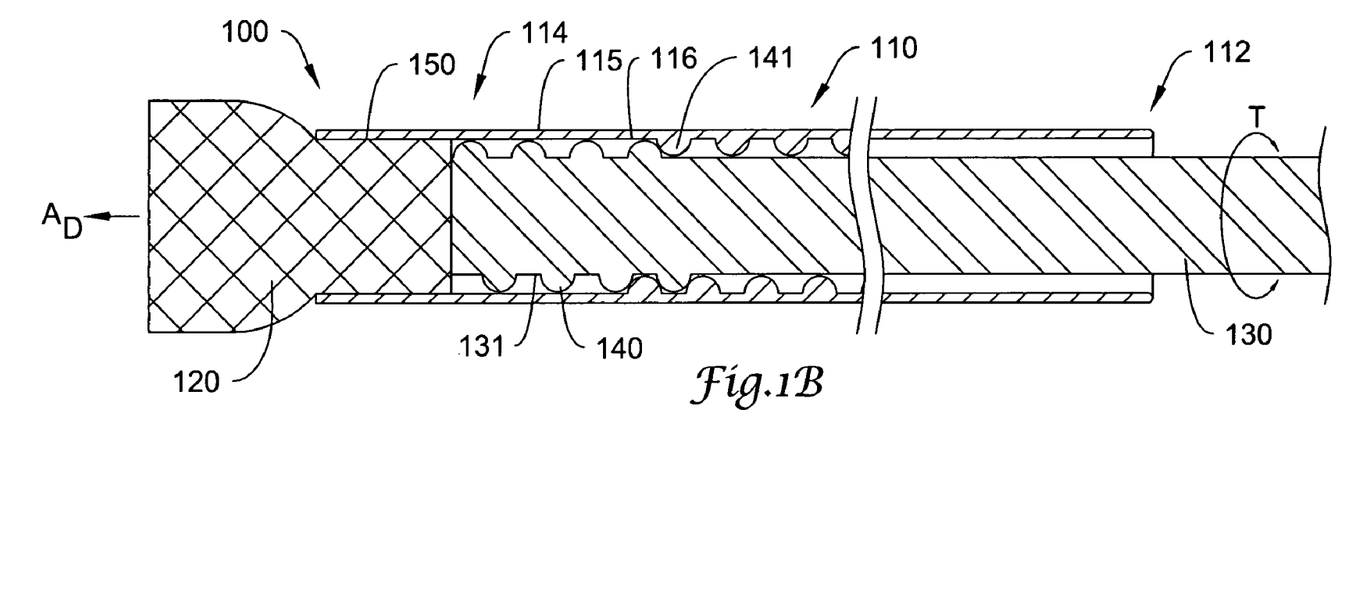
FIG. 1B is a schematic cross-sectional view of the stent delivery assembly of FIG. 1A with a stent partially deployed.

FIG. 1B is a schematic cross-sectional view of FIG. 1A with a stent 120 partially deployed. In this illustrative embodiment, the inner elongate member 130 near the proximal region 112 has been rotated about the longitudinal axis of the inner elongate member 130, causing axial movement of the inner elongate member 130 relative to the elongate member 110 and outer tubular member 115, moving the stent 120 in the distal direction $A_D$. The inner elongate member 130 can move along the longitudinal axis a distance sufficient to deploy the stent 120. The inner elongate member 130 can move along the longitudinal axis a distance at least equal to the length of the stent 120. Thus, using the delivery device 100 described above, a user can carefully control the advancement or deployment of the stent 120 onto the target site.

Figure 2A:
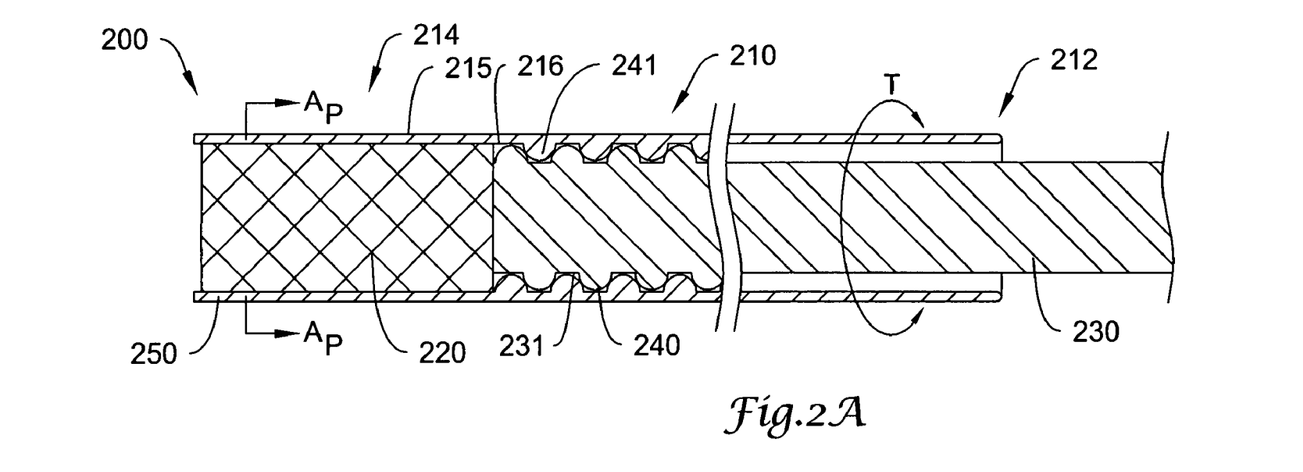
FIG. 2A is a schematic cross-sectional view of another illustrative stent delivery assembly.

FIG. 2A is a schematic cross-sectional view of another illustrative stent delivery assembly 200. The stent delivery assembly 200 can include an elongate member 210. The elongate member 210 can be, for example, a catheter. The elongate member 210 has a proximal region 212 and a distal region 214. At least a portion of proximal region 212 can remain outside of a patient's vasculature. At least a portion of the distal region 214 can remain inside the patient's vasculature. The elongate member 210 is any usable length such as, for example, 10 to 500 cm, 50 to 300 cm, or 75 to 200 cm. The elongate member 210 can be formed of any material suitable for delivering a stent through tortuous vessel passages such as, for example, a polymer, a metal, or a combination thereof. Exemplary materials include polyethylene, reinforced polyethylene, nylon, reinforced nylon, polyurethanes, reinforced polyurethanes, polyamides, or reinforced polyamides.

In an illustrative embodiment, a guidewire can be optionally employed to guide the elongate member 210 distal region 214 to a target site within a patient's vasculature. The guidewire can be within a portion of the elongate member 210. The guidewire can be any operable diameter such as, for example, 0.01 to 0.04 inch or 0.014 to 0.035 inch.

In the illustrative embodiment, the elongate member 210 can have an outer tubular member 215 located at the distal region 214. A self-expanding stent 220 can be disposed within at least a portion of the outer tubular member 215. The outer tubular member 215 has an inner diameter sufficient in size to receive a compressed stent 220. The outer tubular member 215 can be formed of materials similar those described above for forming the elongate member 210. In addition, an optional inner layer 250 of lubricious material can be disposed between the stent 220 and outer tubular member 215. The inner layer 250 can be formed of polytetrafluoroethylene, for example.

In an illustrative embodiment, the outer tubular member 215 can be any material as described above such as, for example, a clear medical grade PTFE (polytetrafluoroethylene) extrusion, which covers the distal 2-20 cm (depending on stent length) of the stent delivery device 200. However, the outer tubular member could be made of any suitable material as described above. A specific alternative embodiment could utilize a fluoropolymer material which is substantially transparent to visible light to enable an operator to directly view deployment in an endoscopic delivery procedure. Such materials are known in the art.

In an illustrative embodiment, self-expanding nitinol stents of from 1-15 mm or 6-14 mm in diameter and ranging from 1-100 mm or 5-50 mm in length can be accommodated. The self-expanding stent 220 can be formed from any material such as, for example, nitinol or stainless steel. The stent 220 can include one or more radiopaque markers for alignment into the target vessel. The stent 220 can be compressed at a low temperature for loading into delivery system 200 and held in its reduced delivery configuration by the outer tubular member 215. In the case of nitinol, upon deployment in vivo at body temperature, the original stent shape can be restored as the nitinol stent self-expands, exerting radial force on the constricted portion of the body lumen to re-establish patency.

The elongate member 210 can include an inner elongate member 230 disposed within at least a portion of the elongate member 210. The inner elongate member 230 can be formed of a polymer, a metal, or a combination thereof, as described above. The inner elongate member 230 can include a helical engagement element 240 on at least a portion of the inner elongate member 230. The helical engagement element 240 can be a helical protrusion extending away from the outer surface 231 of the inner elongate member 230, or the helical engagement element 240 can be a helical channel formed into the outer surface 231 of the inner elongate member 230. A helical engagement element 241 can be on at least a portion of the elongate member 210 inner surface 216. The helical engagement element 241 can be a single protrusion extending away from the elongate member 210 inner surface 216 toward the inner elongate member 230, or the helical engagement element 241 can be a continuous or non-continuous helical protrusion extending away from the elongate member 210 inner surface 216 toward the inner elongate member 230.

Alternatively, the elongate member 210 can include a helical engagement element 240 on at least a portion of the elongate member 210. The helical engagement element 240 can be a helical protrusion extending away from the inner surface 216 of the elongate member 210, or the helical engagement element 240 can be a helical channel formed into the inner surface 216 of the elongate member 210. A helical engagement element 241 can be on at least a portion of the inner elongate member 230 inner surface 231. The helical engagement element 241 can be a single protrusion extending away from the inner elongate member 230 outer surface 231 toward the elongate member 210, or the helical engagement element 241 can be a continuous or non-continuous helical protrusion extending away from the inner elongate member 230 outer surface 231 toward the elongate member 210.

The helical engagement element 241 is arranged and configured to engage the helical engagement element 240 and convert at least a portion of circumferential movement T of the elongate member 210 into axial movement $A_P$. In this embodiment, rotational movement T of the elongate member 210 pulls the outer tubular member 215 axially in a proximal direction $A_P$ relative to the stent 220, deploying the stent.

Figure 2B:
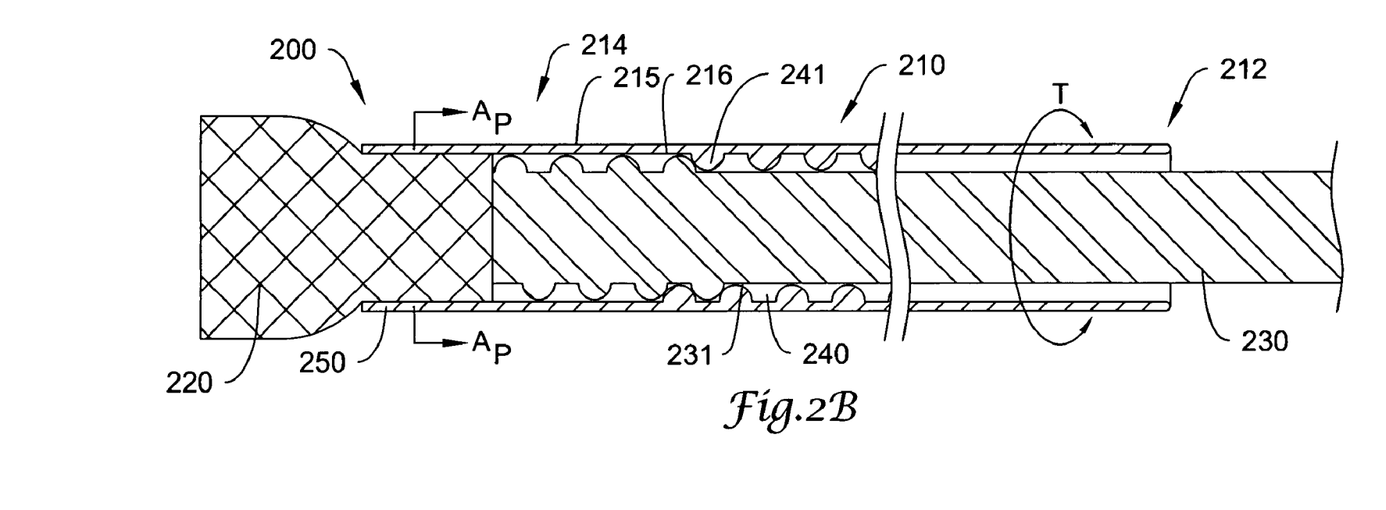
FIG. 2B is a schematic cross-sectional view of the stent delivery assembly of FIG. 2A with a stent partially deployed.

FIG. 2B is a schematic cross-sectional view of FIG. 2A with a stent 220 partially deployed. In this illustrative embodiment, the elongate member 210 proximal region 212 has been rotated about the longitudinal axis of the elongate member 210, causing axial movement of the outer tubular member 215 and/or elongate member 210 relative to the stent 220, moving the outer tubular member 215 in the proximal direction $A_P$. The outer tubular member 215 can move along the longitudinal axis a distance sufficient to deploy the stent 220. The tubular member 215 can move along the longitudinal axis a distance at least equal to the length of the stent 220. Thus, using the delivery device 200 described above, a user can carefully control the deployment of the stent 220 onto the target site.

Figure 3A:
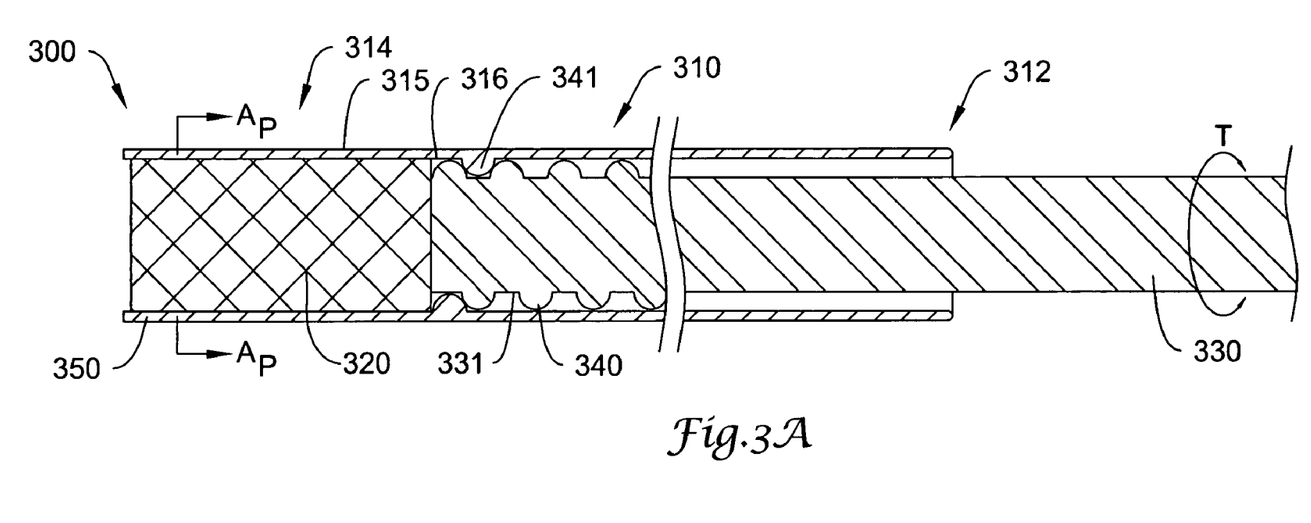
FIG. 3A is a schematic cross-sectional view of another illustrative stent delivery assembly.

FIG. 3A is a schematic cross-sectional view of an illustrative stent delivery assembly 300. The stent delivery assembly 300 can include an elongate member 310. The elongate member 310 can be, for example, a catheter. The elongate member 310 has a proximal region 312 and a distal region 314. At least a portion of proximal region 312 can remain outside of a patient's vasculature. At least a portion of the distal region 314 can remain inside the patient's vasculature. The elongate member 310 is any usable length such as, for example, 10 to 500 cm, 50 to 300 cm, or 75 to 200 cm. The elongate member 310 can be formed of any material suitable for delivering a stent through tortuous vessel passages such as, for example, a polymer, a metal, or a combination thereof. Exemplary materials include polyethylene, reinforced polyethylene, nylon, reinforced nylon, polyurethanes, reinforced polyurethanes, polyamides, or reinforced polyamides.

In an illustrative embodiment, a guidewire can be optionally employed to guide the elongate member 310 distal region 314 to a target site within a patient's vasculature. The guidewire can be within a portion of the elongate member 310. The guidewire can be any operable diameter such as, for example, 0.01 to 0.04 inch or 0.014 to 0.035 inch.

In the illustrative embodiment, the elongate member 310 can have an outer tubular member 315 located at the distal region 314. A self-expanding stent 320 can be disposed within at least a portion of the outer tubular member 315. The outer tubular member 315 has an inner diameter sufficient in size to receive a compressed stent 320. The outer tubular member 315 can be formed of materials similar to those described above for forming the elongate member 310. In addition, an optional inner layer 350 of lubricious material can be disposed between the stent 320 and outer tubular member 315. The inner layer 350 can be formed of polytetrafluoroethylene, for example.

In an illustrative embodiment, the outer tubular member 315 can be any material as described above such as, for example, a clear medical grade PTFE (polytetrafluoroethylene) extrusion, which covers the distal 2-20 cm (depending on stent length) of the stent delivery device 300. However, the outer tubular member could be made of any suitable material as described above. A specific alternative embodiment could utilize a fluoropolymer material which is substantially transparent to visible light to enable an operator to directly view deployment in an endoscopic delivery procedure. Such materials are known in the art.

In an illustrative embodiment, self-expanding nitinol stents of from 1-15 mm or 6-14 mm in diameter and ranging from 1-100 mm or 5-50 mm in length can be accommodated. The self-expanding stent 320 can be formed from any material such as, for example, nitinol or stainless steel. The stent 320 can include one or more radiopaque markers for alignment into the target vessel. The stent 320 can be compressed at a low temperature for loading into delivery system 300 and held in its reduced delivery configuration by the outer tubular member 315. In the case of nitinol, upon deployment in vivo at body temperature, the original stent shape can be restored as the nitinol stent self-expands, exerting radial force on the constricted portion of the body lumen to re-establish patency.

The elongate member 310 can include an inner elongate member 330 disposed within at least a portion of the elongate member 310. The inner elongate member 330 can be formed of a polymer, a metal, or a combination thereof, as described above. The inner elongate member 330 can include a helical engagement element 340 on at least a portion of the inner elongate member 330. The helical element 340 can be a helical protrusion extending away from the outer surface 331 of the inner elongate member 330, or the helical element 340 can be a helical channel formed into the outer surface 331 of the inner elongate member 330. A helical engagement element 341 can be on at least a portion of the elongate member 310 inner surface 316. The helical engagement element 341 can be a single protrusion extending away from the elongate member 310 inner surface 316 toward the inner elongate member 330, or the helical engagement element 341 can be a continuous or non-continuous helical protrusion extending away from the elongate member 310 inner surface 316 toward the inner elongate member 330.

Alternatively, the elongate member 310 can include a helical engagement element 340 on at least a portion of the elongate member 310. The helical element 340 can be a helical protrusion extending away from the inner surface 316 of the elongate member 310, or the helical element 340 can be a helical channel formed into the inner surface 316 of the elongate member 310. A helical engagement element 341 can be on at least a portion of the inner elongate member 330 inner surface 331. The helical engagement element 341 can be a single protrusion extending away from the inner elongate member 330 outer surface 331 toward the elongate member 310, or the helical engagement element 341 can be a continuous or non-continuous helical protrusion extending away from the inner elongate member 330 outer surface 331 toward the elongate member 310.

The helical engagement element 341 is arranged and configured to engage the helical element 340 and convert at least a portion of circumferential movement T of the inner elongate member 330 into axial movement $A_P$. In this embodiment, rotational movement T of the inner elongate member 330 pulls the outer tubular member 315 axially in a proximal direction $A_P$ relative to the stent 320, exposing the stent 320 and deploying the stent 320.

Figure 3B:
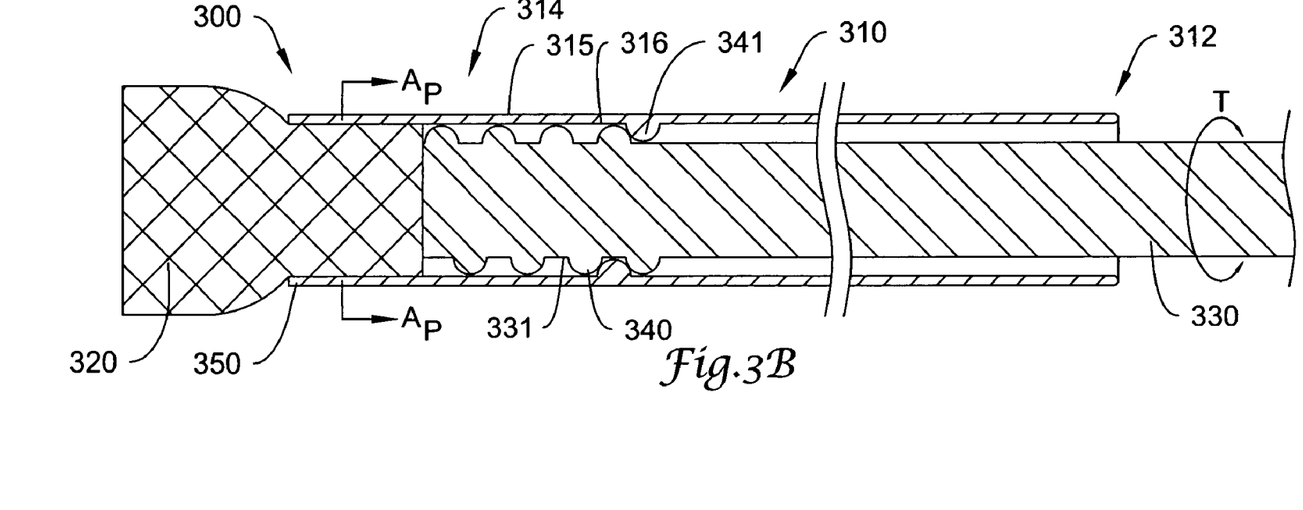
FIG. 3B is a schematic cross-sectional view of the stent delivery assembly of FIG. 3A with a stent partially deployed.

FIG. 3B is a schematic cross-sectional view of FIG. 3A with a stent 320 partially deployed. In this illustrative embodiment, the elongate member 310 near the proximal region 312 has been rotated about the longitudinal axis of the elongate member 330, causing axial movement of the outer tubular member 315 relative to the stent 320, moving the outer tubular member 315 in the proximal direction $A_P$. The outer tubular member 315 can move along the longitudinal axis a distance sufficient to deploy the stent 320. The outer tubular member 315 can move along the longitudinal axis a distance at least equal to the length of the stent 320. Thus, using the delivery device 300 described above, a user can carefully control the deployment of the stent 320 onto the target site.

Figure 4A:
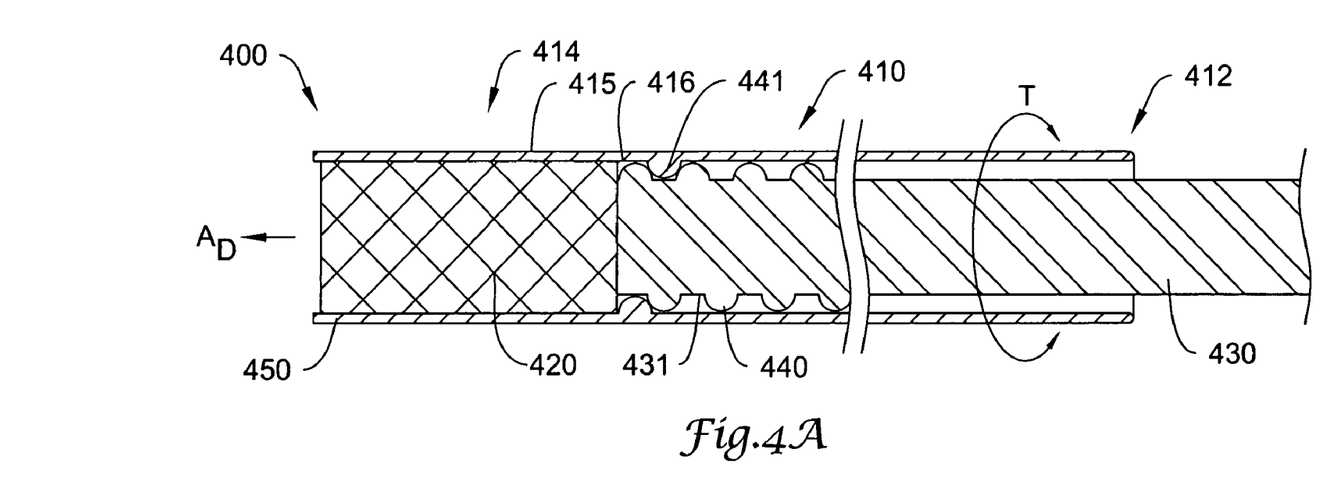
FIG. 4A is a schematic cross-sectional view of an illustrative stent delivery assembly.

FIG. 4A is a schematic cross-sectional view of another illustrative stent delivery assembly 400. The stent delivery assembly 400 can include an elongate member 410. The elongate member 410 can be, for example, a catheter. The elongate member 410 has a proximal region 412 and a distal region 414. At least a portion of proximal region 412 can remain outside of a patient's vasculature. At least a portion of the distal region 414 can remain inside the patient's vasculature. The elongate member 410 is any usable length such as, for example, 10 to 500 cm, 50 to 300 cm, or 75 to 200 cm. The elongate member 410 can be formed of any material suitable for delivering a stent through tortuous vessel passages such as, for example, a polymer, a metal, or a combination thereof. Exemplary materials include polyethylene, reinforced polyethylene, nylon, reinforced nylon, polyurethanes, reinforced polyurethanes, polyamides, or reinforced polyamides.

In an illustrative embodiment, a guidewire can be optionally employed to guide the elongate member 410 distal region 414 to a target site within a patient's vasculature. The guidewire can be within a portion of the elongate member 410. The guidewire can be any operable diameter such as, for example, 0.01 to 0.04 inch or 0.014 to 0.035 inch.

In the illustrative embodiment, the elongate member 410 can have an outer tubular member 415 located at the distal region 414. A self-expanding stent 420 can be disposed within at least a portion of the outer tubular member 415. The outer tubular member 415 has an inner diameter sufficient in size to receive a compressed stent 420. The outer tubular member 415 can be formed of materials similar those described above for forming the elongate member 410. In addition, an optional inner layer 450 of lubricious material can be disposed between the stent 420 and outer tubular member 415. The inner layer 450 can be formed of polytetrafluoroethylene, for example.

In an illustrative embodiment, the outer tubular member 415 can be any material as described above such as, for example, a clear medical grade PTFE (polytetrafluoroethylene) extrusion, which covers the distal 2-20 cm (depending on stent length) of the stent delivery device 400. However, the outer tubular member could be made of any suitable material as described above. A specific alternative embodiment could utilize a fluoropolymer material which is substantially transparent to visible light to enable an operator to directly view deployment in an endoscopic delivery procedure. Such materials are known in the art.

In an illustrative embodiment, self-expanding nitinol stents of from 1-15 mm or 6-14 mm in diameter and ranging from 1-100 mm or 5-50 mm in length can be accommodated. The self-expanding stent 420 can be formed from any material such as, for example, nitinol or stainless steel. The stent 420 can include one or more radiopaque markers for alignment into the target vessel. The stent 420 can be compressed at a low temperature for loading into delivery system 400 and held in its reduced delivery configuration by the outer tubular member 415. In the case of nitinol, upon deployment in vivo at body temperature, the original stent shape can be restored as the nitinol stent self-expands, exerting radial force on the constricted portion of the body lumen to re-establish patency.

The elongate member 410 can include an inner elongate member 430 disposed within at least a portion of the elongate member 410. The inner elongate member 430 can be formed of a polymer, a metal, or a combination thereof, as described above. The inner elongate member 430 can include a helical engagement element 440 on at least a portion of the inner elongate member 430. The helical element 440 can be a helical protrusion extending away from the outer surface 431 of the inner elongate member 430, or the helical element 440 can be a helical channel formed into the outer surface 431 of the inner elongate member 430. A helical engagement element 441 can be on at least a portion of the elongate member 410 inner surface 416. The helical engagement element 441 can be a single protrusion extending away from the elongate member 410 inner surface 416 toward the inner elongate member 430, or the helical engagement element 441 can be a continuous or non-continuous helical protrusion extending away from the elongate member 410 inner surface 416 toward the inner elongate member 430.

Alternatively, the elongate member 410 can include a helical engagement element 440 on at least a portion of the elongate member 410. The helical element 440 can be a helical protrusion extending away from the inner surface 416 of the elongate member 410, or the helical element 440 can be a helical channel formed into the inner surface 416 of the elongate member 410. A helical engagement element 441 can be on at least a portion of the inner elongate member 430 inner surface 431. The helical engagement element 441 can be a single protrusion extending away from the inner elongate member 430 outer surface 431 toward the elongate member 410, or the helical engagement element 441 can be a continuous or non-continuous helical protrusion extending away from the inner elongate member 430 outer surface 431 toward the elongate member 410.

The helical engagement element 441 is arranged and configured to engage the helical element 440 and convert at least a portion of circumferential movement T of the inner elongate member 430 into axial movement $A_D$. In this embodiment, rotational movement T of the inner elongate member 430 forces the stent 420 axially in a distal direction $A_D$ relative to the outer tubular member 415, deploying the stent.

Figure 4B:
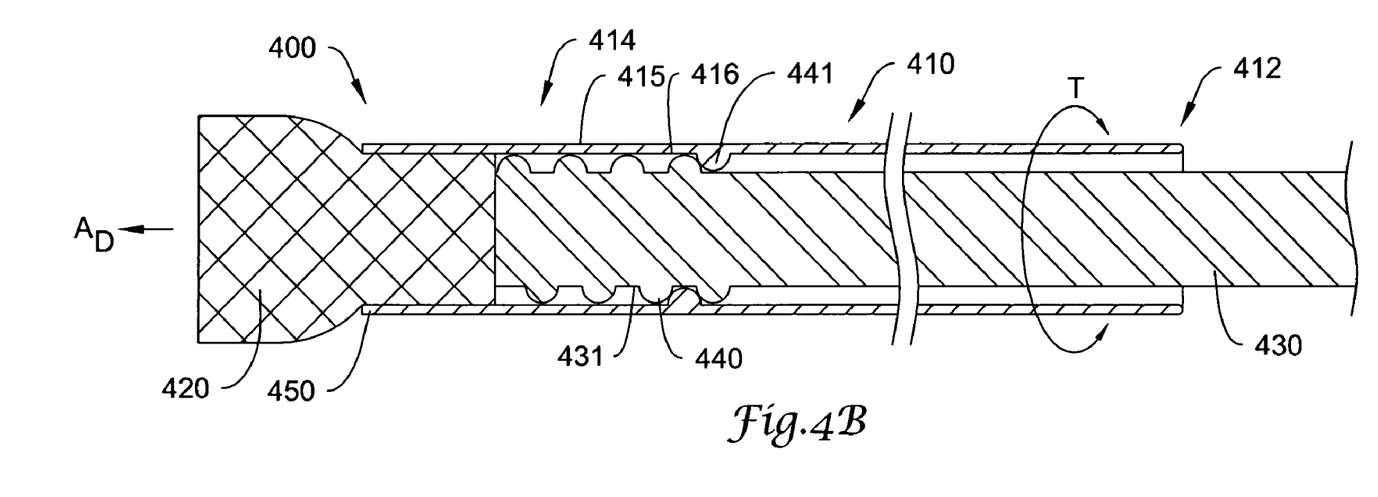
FIG. 4B is a schematic cross-sectional view of the stent delivery assembly of FIG. 4A with a stent partially deployed.

FIG. 4B is a schematic cross-sectional view of FIG. 4A with a stent 420 partially deployed. In this illustrative embodiment, the inner elongate member 430 proximal region 412 has been rotated about the longitudinal axis of the inner elongate member 430, causing axial movement of the inner elongate member 430 and stent 420 relative to the outer tubular member 415, moving the stent 420 in the distal direction $A_D$. The inner tubular member 430 can move along the longitudinal axis a distance sufficient to deploy the stent 420. The inner tubular member 430 can move along the longitudinal axis a distance at least equal to the length of the stent 420. Thus, using the delivery device 400 described above, a user can carefully control the advancement or deployment of the stent 420 onto the target site.

Figure 5A:
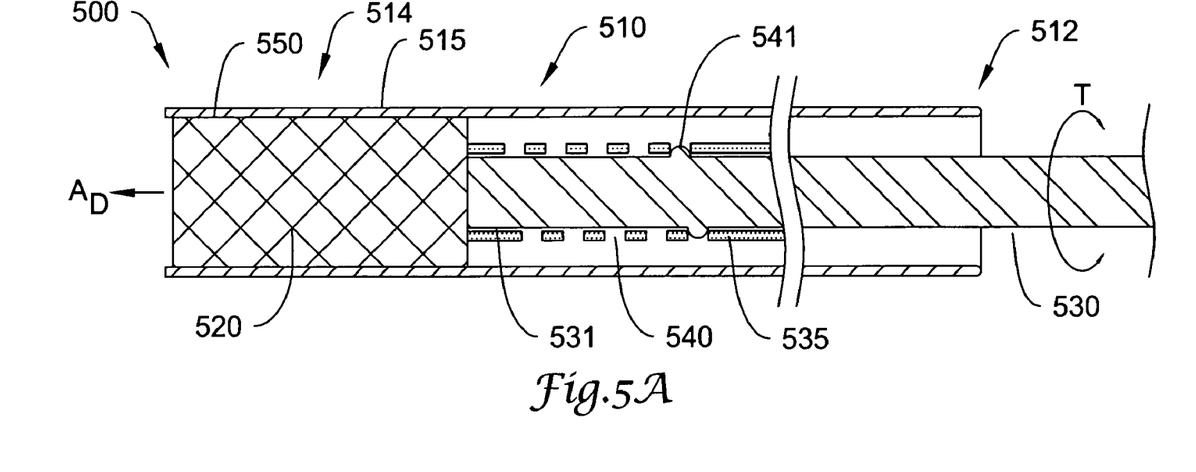
FIG. 5A is a schematic cross-sectional view of an illustrative stent delivery assembly.

FIG. 5A is a schematic cross-sectional view of an illustrative stent delivery assembly 500. The stent delivery assembly 500 can include an elongate member 510. The elongate member 510 can be, for example, a catheter. The elongate member 510 has a proximal region 512 and a distal region 514. At least a portion of proximal region 512 can remain outside of a patient's vasculature. At least a portion of the distal region 514 can remain inside the patient's vasculature. The elongate member 510 is any usable length such as, for example, 10 to 500 cm, 50 to 300 cm, or 75 to 200 cm. The elongate member 510 can be formed of any material suitable for delivering a stent through tortuous vessel passages such as, for example, a polymer, a metal, or a combination thereof. Exemplary materials include polyethylene, reinforced polyethylene, nylon, reinforced nylon, polyurethanes, reinforced polyurethanes, polyamides, or reinforced polyamides.

In an illustrative embodiment, a guidewire can be optionally employed to guide the elongate member 510 distal region 514 to a target site within a patient's vasculature. The guidewire can be within a portion of the elongate member 510. The guidewire can be any operable diameter such as, for example, 0.01 to 0.04 inch or 0.014 to 0.035 inch.

In the illustrative embodiment, the elongate member 510 can have an outer tubular member 515 located at the distal region 514. A self-expanding stent 520 can be disposed within at least a portion of the outer tubular member 515. The outer tubular member 515 has an inner diameter sufficient in size to receive a compressed stent 520. The outer tubular member 515 can be formed of materials similar those described above for forming the elongate member 510. In addition, an optional inner layer 550 of lubricious material can be disposed between the stent 520 and outer tubular member 515. The inner layer 550 can be formed of polytetrafluoroethylene, for example.

In an illustrative embodiment, the outer tubular member 515 can be any material as described above such as, for example, a clear medical grade PTFE (polytetrafluoroethylene) extrusion, which covers the distal 2-20 cm (depending on stent length) of the stent delivery device 500. However, the outer tubular member could be made of any suitable material as described above. A specific alternative embodiment could utilize a fluoropolymer material which is substantially transparent to visible light to enable an operator to directly view deployment in an endoscopic delivery procedure. Such materials are known in the art.

In an illustrative embodiment, self-expanding nitinol stents of from 1-15 mm or 6-14 mm in diameter and ranging from 1-100 mm or 5-50 mm in length can be accommodated. The self-expanding stent 520 can be formed from any material such as, for example, nitinol or stainless steel. The stent 520 can include one or more radiopaque markers for alignment into the target vessel. The stent 520 can be compressed at a low temperature for loading into delivery system 500 and held in its reduced delivery configuration by the outer tubular member 515. In the case of nitinol, upon deployment in vivo at body temperature, the original stent shape can be restored as the nitinol stent self-expands, exerting radial force on the constricted portion of the body lumen to re-establish patency.

The elongate member 510 can include an inner elongate member 530 disposed within at least a portion of the elongate member 510. The inner elongate member 530 can be formed of a polymer, a metal, or a combination thereof, as described above. The inner elongate member 530 can include a helical engagement element 541 on at least a portion of the inner elongate member 530. The helical engagement element 541 can be a helical protrusion extending away from the outer surface 531 of the inner elongate member 530.

An intermediate tubular member 535 can be disposed between the inner tubular member 530 and the elongate member 510. The intermediate tubular member 535 can be formed of any material described above. In an illustrative embodiment, the intermediate tubular member can be a hypotube. A helical element 540 can be on at least a portion of the intermediate tubular member 535. The helical element 540 can be a continuous or non-continuous helical protrusion or channel.

Alternatively, the intermediate tubular member 535 can include a helical element 540 on at least a portion of the intermediate tubular member 535. The helical element 540 can be a helical protrusion extending away from the inner surface of the intermediate tubular member 535, or the helical element 540 can be a helical channel formed into the tubular member 535. A helical engagement element 541 can be on at least a portion of the inner elongate member 530 inner surface 531. The helical engagement element 541 can be a single protrusion extending away from the inner elongate member 530 outer surface 531 toward the intermediate tubular member 535, or the helical engagement element 541 can be a continuous or non-continuous helical protrusion extending away from the inner elongate member 530 outer surface 531 toward the intermediate tubular member 535.

The helical engagement element 541 is arranged and configured to engage the helical element 540 and convert at least a portion of circumferential movement T of the inner elongate member 530 into axial movement $A_D$. The inner elongate member 530 acts as a torque plunger when advanced. In this embodiment, rotational movement T of the inner elongate member 530 forces the inner elongate member 530 and/or the intermediate tubular member 535 against the self-expanding stent 520 and pushes the self-expanding stent 520 axially in a distal direction $A_D$ relative to the outer tubular member 515, deploying the stent.

Figure 5B:
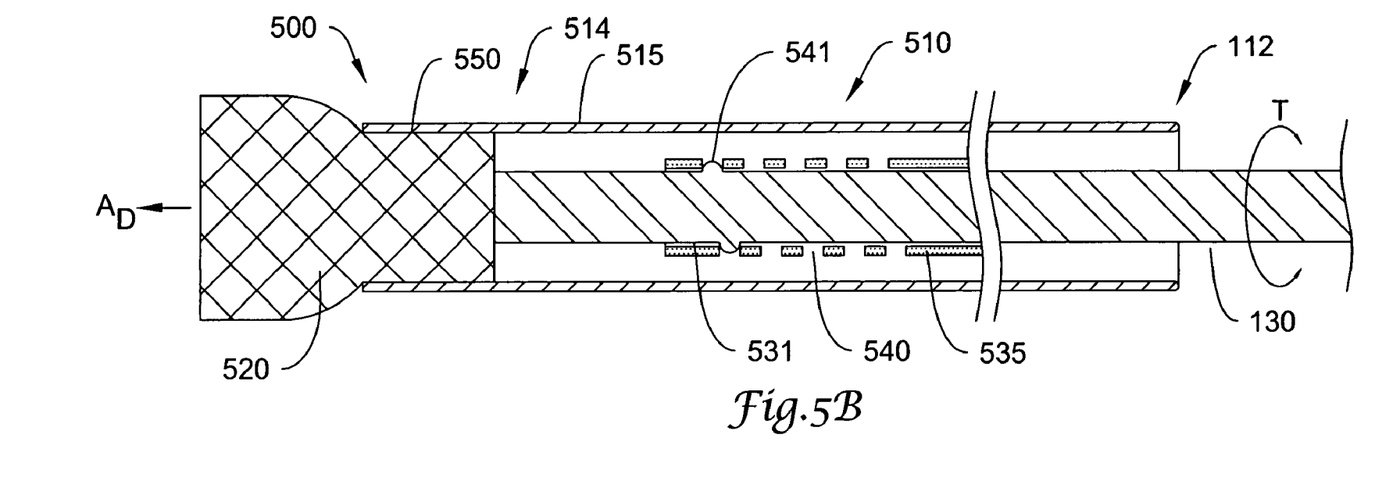
FIG. 5B is a schematic cross-sectional view of the stent delivery assembly of FIG. 5A with a stent partially deployed.

FIG. 5B is a schematic cross-sectional view of FIG. 5A with a stent 520 partially deployed. In this illustrative embodiment, the inner elongate member 530 near the proximal region 512 has been rotated about the longitudinal axis of the inner elongate member 530, causing axial movement of the inner elongate member 530 and/or intermediate tubular member 535 relative to the elongate member 510 and outer tubular member 515, moving the stent 520 in the distal direction $A_D$. The inner elongate member 530 and/or intermediate tubular member 535 can move along the longitudinal axis a distance sufficient to deploy the stent 520. The inner elongate member 530 and/or intermediate tubular member 535 can move along the longitudinal axis a distance at least equal to the length of the stent 520. Thus, using the delivery device 500 described above, a user can carefully control the advancement or deployment of the stent 520 onto the target site.

Figure 6:
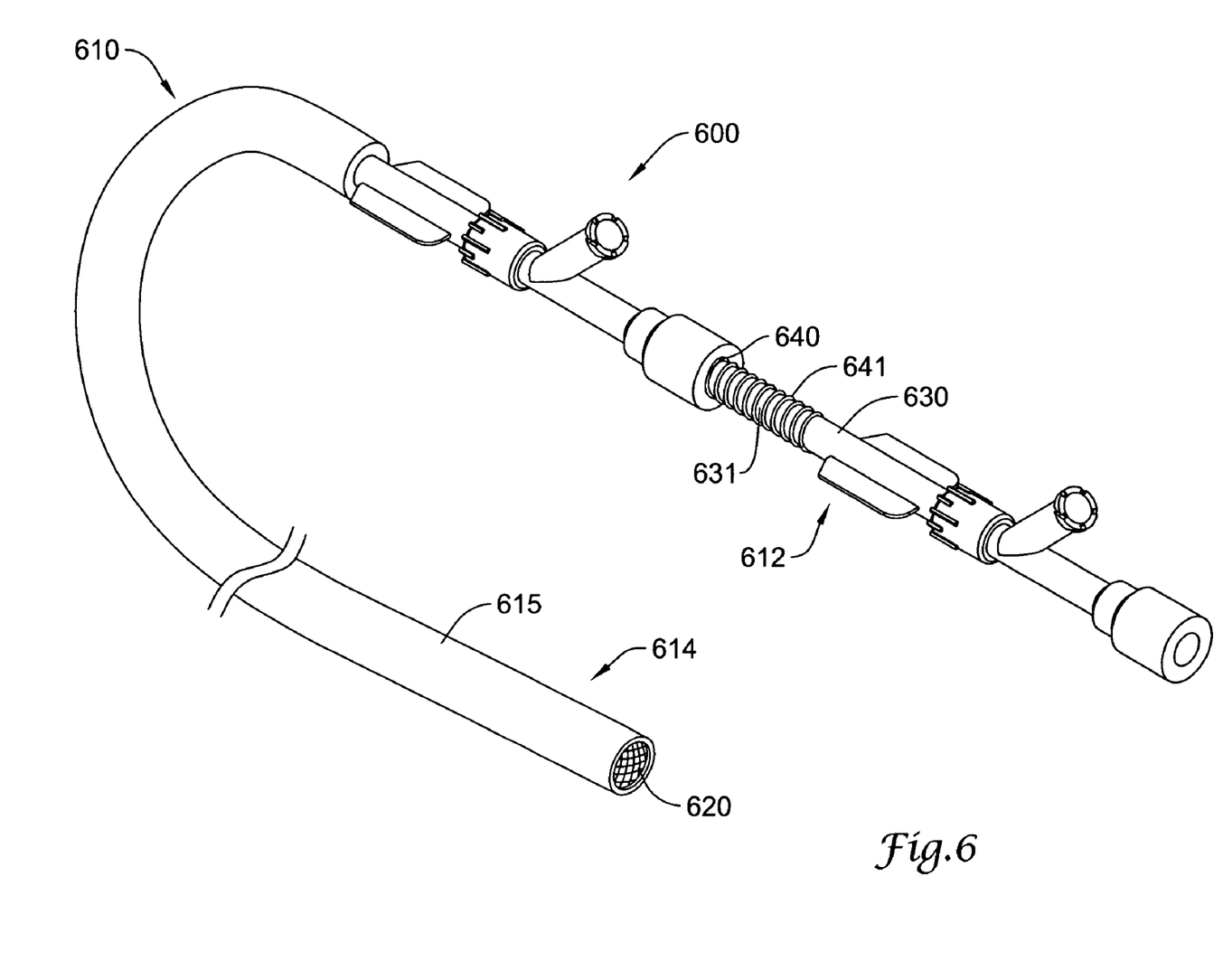
FIG. 6 is a perspective view of an illustrative stent delivery assembly.

FIG. 6 is a perspective view of an illustrative stent delivery 600 assembly. The stent delivery assembly 600 can include an elongate member 610. The elongate member 610 can be, for example, a catheter. The elongate member 610 has a proximal region 612 and a distal region 614. At least a portion of proximal region 612 can remain outside of a patient's vasculature. At least a portion of the distal region 614 can remain inside the patient's vasculature. The elongate member 610 is any usable length such as, for example, 10 to 500 cm, 50 to 300 cm, or 75 to 200 cm. The elongate member 610 can be formed of any material suitable for delivering a stent through tortuous vessel passages such as, for example, a polymer, a metal, or a combination thereof. Exemplary materials include polyethylene, reinforced polyethylene, nylon, reinforced nylon, polyurethanes, reinforced polyurethanes, polyamides, or reinforced polyamides.

In the illustrative embodiment, the elongate member 610 can have an outer tubular member 615 located at the distal region 614. A self-expanding stent 620 can be disposed within at least a portion of the outer tubular member 615. The outer tubular member 615 has an inner diameter sufficient in size to receive a compressed stent 620. The outer tubular member 615 can be formed of materials similar those described above for forming the elongate member 610.

In an illustrative embodiment, the outer tubular member 615 can be any material as described above such as, for example, a clear medical grade PTFE (polytetrafluoroethylene) extrusion, which covers the distal 2-20 cm (depending on stent length) of the stent delivery device 600. However, the outer tubular member could be made of any suitable material as described above.

In an illustrative embodiment, self-expanding nitinol stents of from 1-15 mm or 6-14 mm in diameter and ranging from 1-100 mm or 5-50 mm in length can be accommodated. The self-expanding stent 620 can be formed from any material such as, for example, nitinol or stainless steel. The stent 620 can include one or more radiopaque markers for alignment into the target vessel. The stent 620 can be compressed at a low temperature for loading into delivery system 600 and held in its reduced delivery configuration by the outer tubular member 615. In the case of nitinol, upon deployment in vivo at body temperature, the original stent shape can be restored as the nitinol stent self-expands, exerting radial force on the constricted portion of the body lumen to re-establish patency.

The elongate member 610 can include an inner elongate member 630 disposed within at least a portion of the elongate member 610. The inner elongate member 630 can be formed of a polymer, a metal, or a combination thereof, as described above. The inner elongate member 630 can include a helical engagement element 641 on at least a portion of the inner elongate member 630. The helical engagement element 641 can be a helical protrusion extending away from the outer surface 631 of the inner elongate member 630. In this embodiment, the helical engagement element 641 is disposed on the proximal end 612 of the inner elongate member 630. However, the helical engagement element 641 may be located on any position along the inner elongate member 630.

The helical engagement element 641 is arranged and configured to engage the helical element 640 and convert at least a portion of circumferential movement of the inner elongate member 630 into axial movement. In this embodiment, rotational movement of the inner elongate member 630 pulls the outer tubular member in a proximal direction relative to the inner elongate member 630, deploying the stent as described in FIGS. 2 and 3 above.

Figure 7:
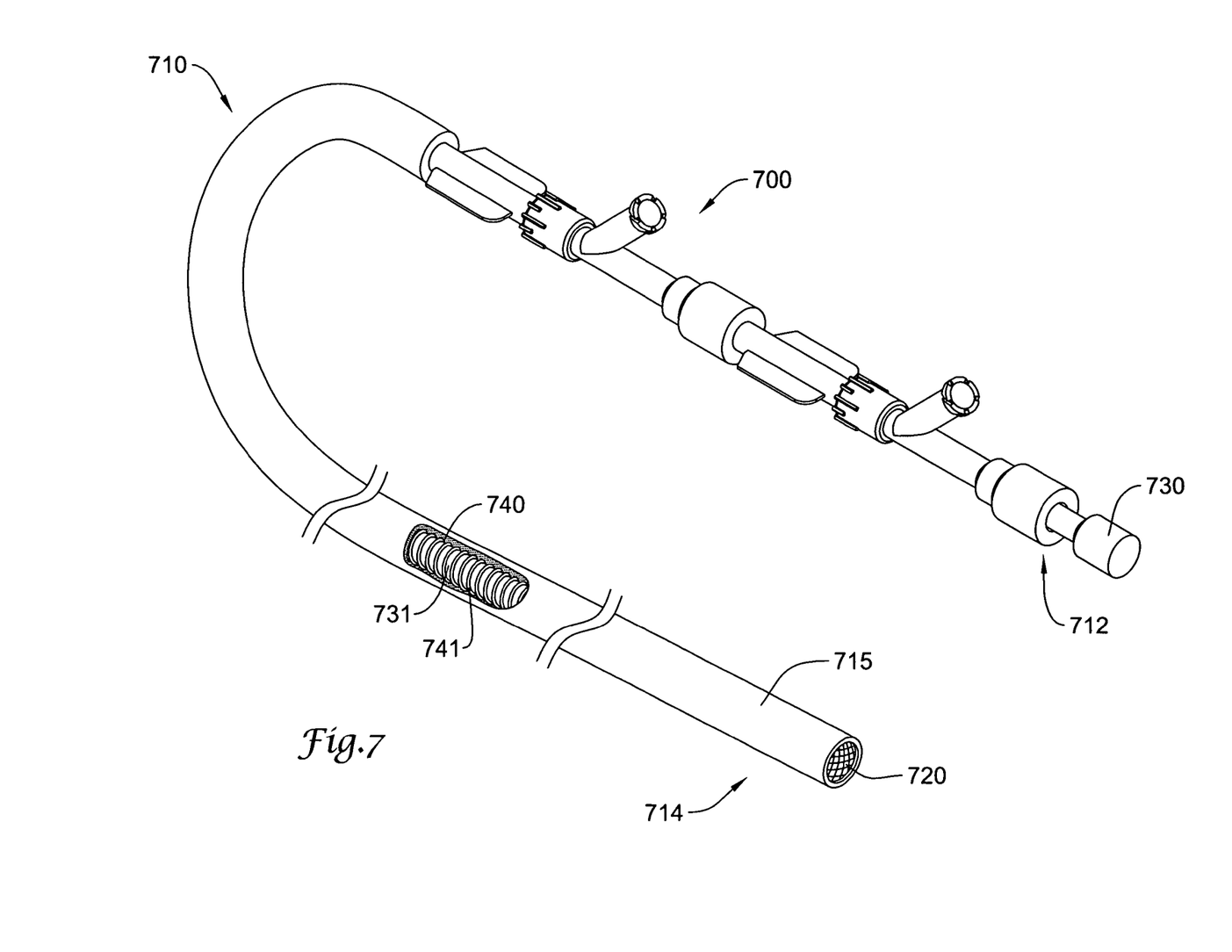
FIG. 7 is a perspective view of another illustrative stent delivery assembly.

FIG. 7 is a perspective view of another illustrative stent delivery 700 assembly. The elongate member 710 can be, for example, a catheter. The elongate member 710 has a proximal region 712 and a distal region 714. At least a portion of proximal region 712 can remain outside of a patient's vasculature. At least a portion of the distal region 714 can remain inside the patient's vasculature. The elongate member 710 is any usable length such as, for example, 10 to 500 cm, 50 to 300 cm, or 75 to 200 cm. The elongate member 710 can be formed of any material suitable for delivering a stent through tortuous vessel passages such as, for example, a polymer, a metal, or a combination thereof. Exemplary materials include polyethylene, reinforced polyethylene, nylon, reinforced nylon, polyurethanes, reinforced polyurethanes, polyamides, or reinforced polyamides.

In the illustrative embodiment, the elongate member 710 can have an outer tubular member 715 located at the distal region 714. A self-expanding stent 720 can be disposed within at least a portion of the outer tubular member 715. The outer tubular member 715 has an inner diameter sufficient in size to receive a compressed stent 720. The outer tubular member 715 can be formed of materials similar those described above for forming the elongate member 710.

In an illustrative embodiment, the outer tubular member 715 can be any material as described above such as, for example, a clear medical grade PTFE (polytetrafluoroethylene) extrusion, which covers the distal 2-20 cm (depending on stent length) of the stent delivery device 700. However, the outer tubular member could be made of any suitable material as described above.

In an illustrative embodiment, self-expanding nitinol stents of from 1-15 mm or 6-14 mm in diameter and ranging from 1-100 mm or 5-50 mm in length can be accommodated. The self-expanding stent 720 can be formed from any material such as, for example, nitinol or stainless steel. The stent 720 can include one or more radiopaque markers for alignment into the target vessel. The stent 720 can be compressed at a low temperature for loading into delivery system 700 and held in its reduced delivery configuration by the outer tubular member 715. In the case of nitinol, upon deployment in vivo at body temperature, the original stent shape can be restored as the nitinol stent self-expands, exerting radial force on the constricted portion of the body lumen to re-establish patency.

The elongate member 710 can include an inner elongate member 730 disposed within at least a portion of the elongate member 710. The inner elongate member 730 can be formed of a polymer, a metal, or a combination thereof, as described above. The inner elongate member 730 can include a helical engagement element 741 on at least a portion of the inner elongate member 730 (shown on FIG. via cutaway window). The helical engagement element 741 can be a helical protrusion extending away from the outer surface 731 of the inner elongate member 730.

The helical engagement element 741 is arranged and configured to engage the helical element 740 and convert at least a portion of circumferential movement of the inner elongate member 730 into axial movement. In this embodiment, rotational movement of the inner elongate member 730 forces the inner elongate member 730 against the self-expanding stent 720 and pushes the self-expanding stent 720 axially in a distal direction relative to the outer tubular member 715, deploying the stent, as described above.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A self-expanding stent delivery assembly comprising:
    an elongate member having a proximal region and a distal region, the proximal region including a hub assembly, the distal region having an outer tubular member having an inner surface and a distal end, the elongate member further including an inner elongate member disposed within the outer tubular member, the inner elongate member having an outer surface;
        wherein the inner elongate member is stationary relative to the hub assembly;
        wherein the outer tubular member is configured to be rotatable about a longitudinal axis of the inner elongate member, wherein rotational movement of the outer tubular member causes the distal end of the outer tubular member to move axially in a proximal direction toward the hub assembly such that the distance between the distal end of the outer tubular member and the hub assembly is variable;
        a first engagement member disposed along the inner surface of the outer tubular member;
        a second engagement member disposed along the outer surface of the inner elongate member, the second engagement member extending from a distal end of the inner elongate member towards a proximal end of the inner elongate member, the first engagement member interacting with the second engagement member;
        wherein at least one of the first and second engagement members comprises a helical element
        a self-expanding stent being expandable from a compressed delivery configuration to an expanded deployed configuration, the self-expanding stent disposed within the outer tubular member and held in the compressed delivery configuration by engagement with the inner surface of the outer tubular member such that the outer tubular member restricts expansion of the self-expanding stent;
        wherein a proximal end of the self-expanding stent abuts the distal end of the inner elongate member at the same position from where the second engagement member extends towards the proximal end of the inner elongate member;
        wherein rotational movement of the outer tubular member causes axial movement of the distal end of the outer tubular member toward the hub assembly, deploying the stent out from the outer tubular member, whereby the self-expanding stent automatically reverts to the expanded deployed configuration upon deployment out from the outer tubular member.

2. The assembly according to claim 1, further comprising a layer of lubricious material disposed on the inner surface of the outer tubular member between the outer tubular member and the self-expanding stent.

3. The assembly according to claim 1, wherein the helical element comprises a helical projection extending out from the inner surface of the outer tubular member.

4. The assembly according to claim 1, wherein the helical element comprises a helical channel formed in the inner surface of the outer tubular member.

5. The assembly according to claim 4, wherein the helical element comprises a helical projection extending out from the outer surface of the inner elongate member.

6. The assembly according to claim 3, wherein the helical element comprises a helical channel formed in the outer surface of the inner elongate member.

7. The assembly according to claim 1, wherein the outer tubular member comprises PTFE.

8. A self-expanding stent delivery assembly comprising:
    an elongate member having a proximal region and a distal region, the proximal region including a hub assembly, the distal region having an outer tubular member having a distal end, the elongate member further including an inner elongate member disposed within the outer tubular member;
        wherein the inner elongate member is stationary relative to the hub assembly;
        wherein the outer tubular member is configured to be rotatable about a longitudinal axis of the inner elongate member, wherein rotational movement of the outer tubular member causes the distal end of the outer tubular member to move axially in a proximal direction toward the hub assembly such that the distance between the distal end of the outer tubular member and the hub assembly is variable;
        either a helical element disposed on at least a portion of the inner elongate member from a distal end of the inner elongate member towards a proximal end of the inner elongate member engaged with a helical element engagement member disposed on at least a portion of the outer tubular member; and a self-expanding stent being expandable from a compressed delivery configuration to an expanded deployed configuration, the self-expanding stent disposed within the outer tubular member and held in the compressed delivery configuration by engagement with an inner surface of the outer tubular member such that the outer tubular member restricts expansion of the self-expanding stent;

wherein a proximal end of the self-expanding stent abuts the distal end of the inner elongate member at the same position from where the helical element of the inner elongate member extends towards the proximal end of the inner elongate member;

wherein rotational movement of the outer tubular member causes axial movement of the distal end of the outer tubular member toward the hub assembly, deploying the stent out from the outer tubular member, whereby the self-expanding stent automatically reverts to the expanded deployed configuration upon deployment out from the outer tubular member.

9. The assembly according to claim 8, wherein the outer tubular member comprises PTFE.

* * * * *